United States Patent
Shayani

(10) Patent No.: US 7,686,822 B2
(45) Date of Patent: Mar. 30, 2010

(54) HERNIA REPAIR METHOD

(76) Inventor: Vafa Shayani, 110 North Quincy St., Hinsdale, IL (US) 60521

( * ) Notice: Subject to any disclaimer, the term of this patent is extended or adjusted under 35 U.S.C. 154(b) by 484 days.

(21) Appl. No.: 11/753,303

(22) Filed: May 24, 2007

(65) Prior Publication Data

US 2007/0219569 A1  Sep. 20, 2007

Related U.S. Application Data

(62) Division of application No. 10/436,812, filed on May 13, 2003, now abandoned.

(51) Int. Cl.
*A61B 17/08* (2006.01)

(52) U.S. Cl. ........................... 606/151; 606/156
(58) Field of Classification Search ............... 623/23.72, 623/17.19, 23.54; 606/70, 285, 151–156; 128/898
See application file for complete search history.

(56) References Cited

U.S. PATENT DOCUMENTS

| | | | |
|---|---|---|---|
| 5,282,616 | A | 2/1994 | Stacavich-Notaro |
| 5,384,939 | A | 1/1995 | Weber |
| 5,697,979 | A | * 12/1997 | Pignataro ................. 623/15.11 |
| D390,099 | S | 2/1998 | Bailey et al. |
| 5,728,116 | A | 3/1998 | Rosenman |
| 5,972,022 | A | 10/1999 | Huxel |
| 6,036,701 | A | 3/2000 | Rosenman |
| 6,735,819 | B2 | 5/2004 | Iverson et al. |

* cited by examiner

*Primary Examiner*—(Jackie) Tan-Uyen T Ho
*Assistant Examiner*—Christina Lauer
(74) *Attorney, Agent, or Firm*—Boyle Fredrickson, SC

(57) ABSTRACT

An article of manufacture suitable for positioning a sheet of mesh material over tissue is described. In one embodiment, the article comprises a surgical tack having a hook-type material such as Velcro® material carried by the tack, e.g., secured to the top of the head thereof. A plurality of such tacks are positioned around the site of a hernia or the like and the mesh is positioned over the site and the tacks. The mesh is made of a loop-type Velcro® material or the like which allows the mesh to be releasably engaged and disengaged from the hook-type material carried by the tacks so that the mesh can be appropriately positioned over the tissue.

17 Claims, 3 Drawing Sheets

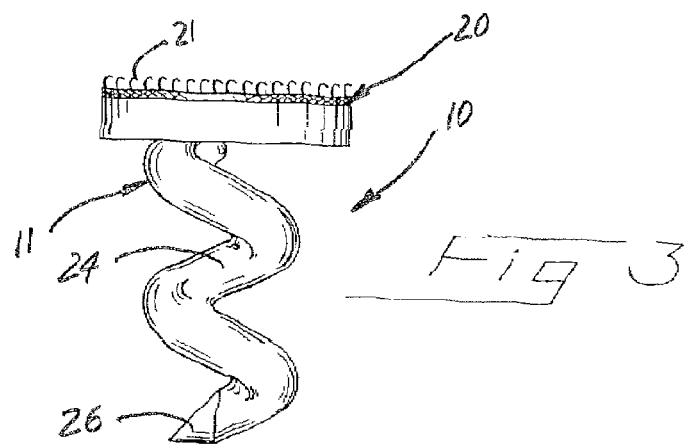
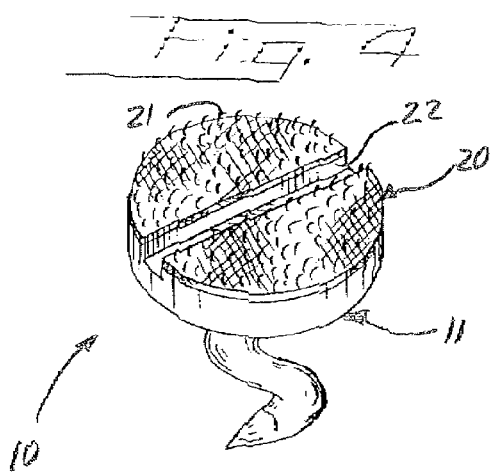
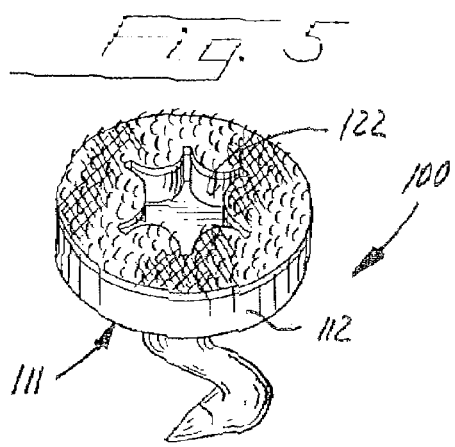
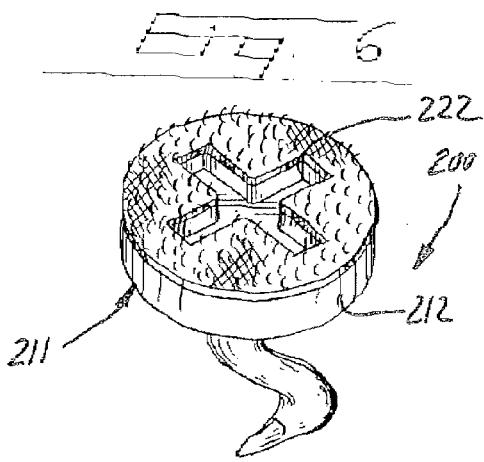
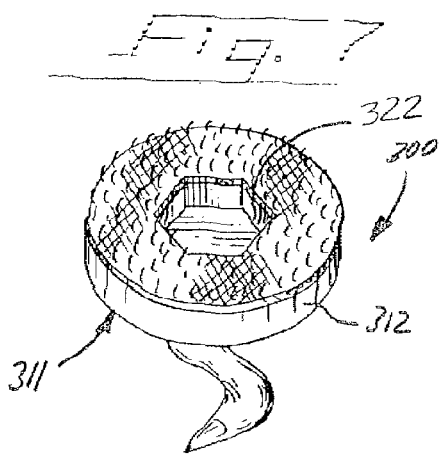

HERNIA REPAIR METHOD

CROSS-REFERENCE TO RELATED APPLICATIONS

This application is a divisional application and claims priority to U.S. application Ser. No. 10/436,812, filed on May 13, 2003 now abandoned, titled "Article for positioning mesh over tissue", which was published on Nov. 18, 2004 as U.S. Patent Application Publication No. 2004/0230208 and the disclosure of which is incorporated herein.

FIELD OF THE INVENTION

This invention relates to surgical devices and, more particularly, to surgical articles used to position and fix mesh over tissue for repair of abdominal wall defects.

BACKGROUND OF THE INVENTION

Abdominal wall defects or hernias are commonly repaired using a physiologically compatible synthetic mesh such as a polytetrafluoroethylene mesh, polypropylene mesh, and the like. Tension-free mesh repair of hernias is preferred over conventional suture closure, which often results in the creation of significant tension and subsequent recurrence of the hernia. More recently, video-assisted (laparoscopic) technology has been utilized to repair the abdominal wall defects from a posterior (from inside the abdomen) position, thus offering the potential for a lower incidence of subsequent recurrence of the hernia. Where the laparoscopic technique is utilized, the synthetic mesh is typically secured against the abdominal wall using surgical tacks of various types, for example of the type disclosed in U.S. Pat. Nos. 5,728,116 and 6,036,701, and also of the Q-ring type commercially available from Onux Medical, Inc. of Hampton, N.H.

One of the challenges encountered during laparoscopic hernia repair is the placement of the mesh and the tacks in the precisely intended location to provide adequate overlap of the mesh with the surrounding abdominal wall tissue. With each application of an additional surgical tack, repositioning of the mesh (when necessary) becomes more and more difficult, if not impossible. In addition, during the early process of tacking the mesh to the abdominal wall, the field of view is often significantly hindered by the partially dangling piece of mesh. This limitation may reach unsafe levels in cases of large abdominal wall defects requiring large pieces of mesh, with significant potential for inadvertent injury to abdominal organs.

There is, therefore, a need for improving the existing technique of laparoscopic hernia repair through the use of a tack or the like that would allow placement of the tacks before obliteration of the view by the mesh, and subsequent near-perfect positioning and repositioning of the mesh as needed.

SUMMARY OF THE INVENTION

The present invention provides a safe and efficient means or article for the application and subsequent repositioning of synthetic mesh to the abdominal wall with minimal risk of injury to abdominal tissue and organs.

Accordingly, the invention is an article suitable for positioning a sheet of surgical mesh over tissue and comprising a mesh engaging material associated with a tack adapted to be fastened to the tissue. The mesh is releasably engaged and disengaged from the mesh engaging material associated with the tack so as to allow the positioning and subsequent repositioning and stretching of the mesh over the tissue.

In one embodiment, the tack includes a head bearing a hook-type fiber material and a tissue anchoring member which depends from the head. The tack is secured to the tissue and the mesh material is releasably engageable with the hook-type material carried by the tack. In this manner the mesh material can be positioned and repositioned over tissue as desired by the surgeon.

In another embodiment, the tack secures a piece of the mesh engaging material to the tissue. The mesh can then be pressed against the mesh engaging material secured to the tissue and is releasably held in place by the mesh engaging material.

Other advantages and features of the present invention will be more readily apparent from the following detailed description of the preferred embodiments of the invention, the accompanying drawings, and the appended claims.

BRIEF DESCRIPTION OF THE DRAWINGS

In the accompanying drawings forming part of the specification and in which like numerals are employed to designate like parts throughout the same.

FIG. 3 is a front elevational view of the entire surgical tack of FIG. 1;

FIG. 4 is a perspective view of the surgical tack of FIG. 3 provided with a slotted head;

FIG. 5 is a perspective view of a tack similar to that of FIG. 3 and provided with a head configured to receive a Torx driver;

FIG. 6 is a perspective view of a tack similar to that of FIG. 3 and configured to receive a Phillips driver;

FIG. 7 is a perspective view of a tack similar to that of FIG. 3 and configured to receive an Allen driver.

DETAILED DESCRIPTION OF THE PREFERRED EMBODIMENTS

Figure 1:
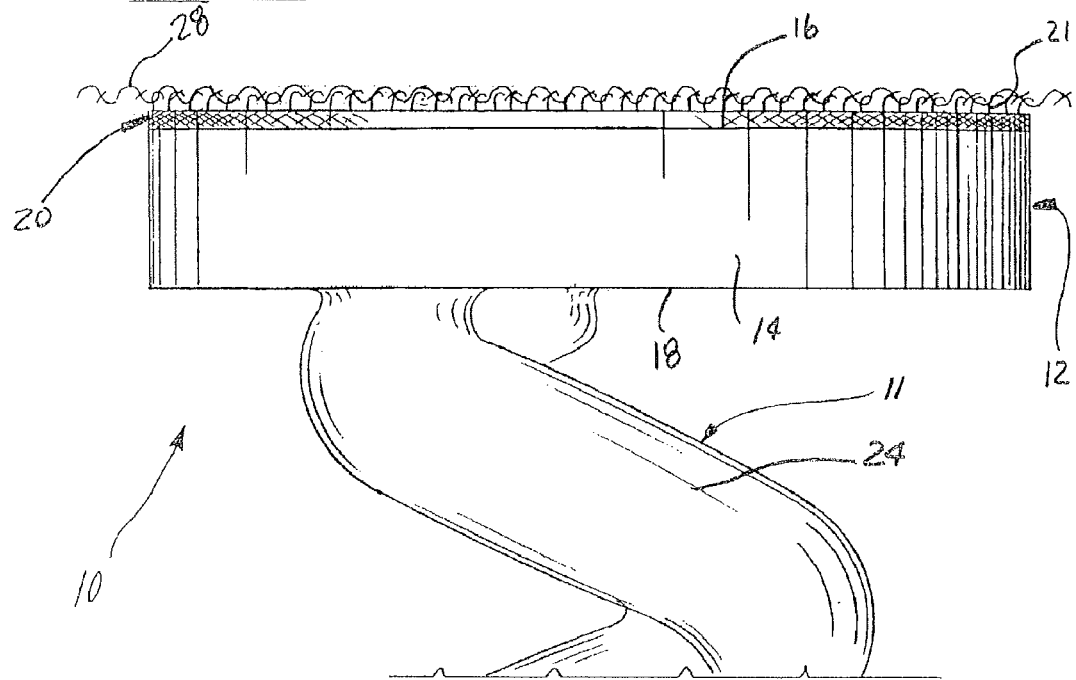
FIG. 1 is an enlarged, partial front elevational view of a surgical tack provided with releasable mesh engagement element.

The invention disclosed herein is susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

Moreover, it is understood that the specification herein does not necessarily describe the details of the surgical tack or the releasable mesh engagement element that are known in the art and that will be recognized as such by those skilled in the art. The detailed descriptions of these elements are not necessary to an understanding of the article of the present invention. Accordingly, such elements are herein represented and described only to the degree necessary to aid in an understanding of the features of the present invention.

FIGS. 1, 3 and 4 depict a preferred embodiment of the present invention in which article 10 comprises a surgical tack 11 having a releasable mesh engagement element or member 20 attached to the top of head 12.

Head 12 has a circular, disk like figuration and includes a body 14 and top and bottom radial faces 16 and 18, respectively. The top face 16 of the head 12 is covered with a circular, disk shaped releasable mesh engagement member, such as patch 20, which is preferably made of and includes hook-type Velcro® or the like latching fiber material 21. The mesh engagement member such as patch 20 may be secured to the top face 16 of the head 12 by any known means including, but not limited to, adhesive applied either directly to the top of the head 12, to the lower surface of the mesh engagement member 20, or both. A tack driver cavity, such as slot or straight slit 22, extends across top face 16 and into the body 14 of head 12. The slot 22 is configured to receive a complementary driver.

The tack 11 additionally comprises an elongate spiral screw member or base 24 which extends generally away from the bottom radial face 18 of the head 12. The spiral screw member 24 terminates in a distal tissue piercing tip 26.

FIGS. 5-7 depict alternate respective article embodiments 100, 200 and 300 similar in structure to the article 10 except that the respective heads 112, 212 and 312 of the tacks 111, 211 and 311 respectively incorporate cavities 122, 222 and 322 structured and shaped to accept Torx, Phillips or Allen drivers for driving and securing the tacks into tissue for the purposes described in more detail below.

The article 10 of the present invention is suitable for use in a variety of surgical procedures including, but not limited to, the repair of ventral hernias. In connection with the repair of ventral hernias, an incision is first made into a patient's abdominal cavity in order to access the site of the hernia (i.e., abdominal wall defect) using conventional surgical techniques. After the site has been prepared using conventional surgical techniques, several tacks capable of releasably holding a surgical mesh are secured around the perimeter of the abdominal wall defect using conventional tacking devices such as, for example, a surgical grasper, a tack driver, or alternatively, a tacking gun which has been pre-loaded with a predetermined number of the surgical tacks.

Figure 2:
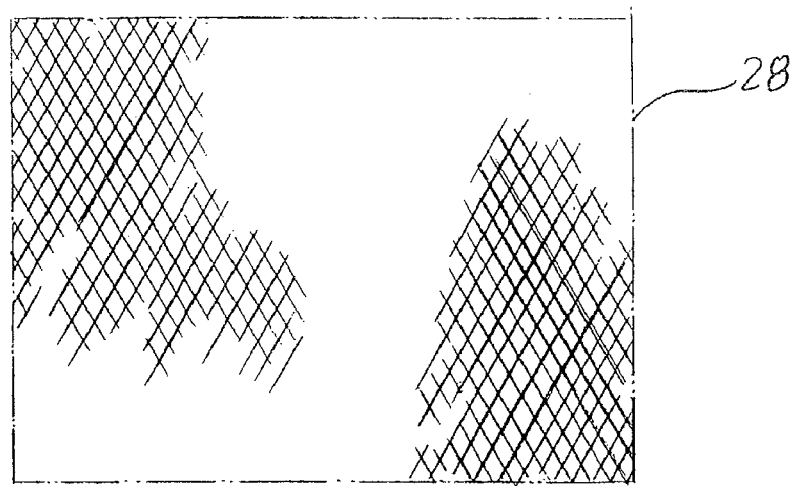
FIG. 2 is a top plan view of a patch of surgical mesh suitable for releasable engagement to the mesh engagement element shown in FIG. 1.

The tacks 11 are advantageously secured to the tissue around the abdominal wall defect sought to be repaired prior to the insertion of any mesh material into the abdominal cavity, and with the full view of the abdominal wall defect and surrounding internal organs. Thereafter, an appropriately sized sheet or patch of the biocompatible surgical mesh, for example, such as the sheet of mesh material 28 depicted in FIG. 2, is inserted through the incision and positioned over the site of the hernia with the peripheral edges thereof overlying the tacks. The mesh material is then pressed into abutting contact against the tacks 11 and, more specifically, against the heads 12 thereof so as to cause the loop-type material comprising the fabric of the mesh 28 to become releasably intertwined, latched and engaged with the hook-type material 21 of tack 11 as shown in FIG. 1. The mesh 28 may then be selectively disengaged or released from tack 11, and then subsequently selectively stretched and re-attached or re-engaged with the latching fiber material until the optimal positioning and stretching of the mesh 28 over the tissue site has been achieved.

Once the desired mesh placement has been accomplished, any one of a number of conventional tacking devices may be used to apply conventional surgical tacks to further secure and maintain the mesh 28 over the site of the hernia. The hernia repair procedure is then completed in a conventional manner and the incision in the wall of the abdominal cavity is closed using conventional surgical sutures.

Figure 8:
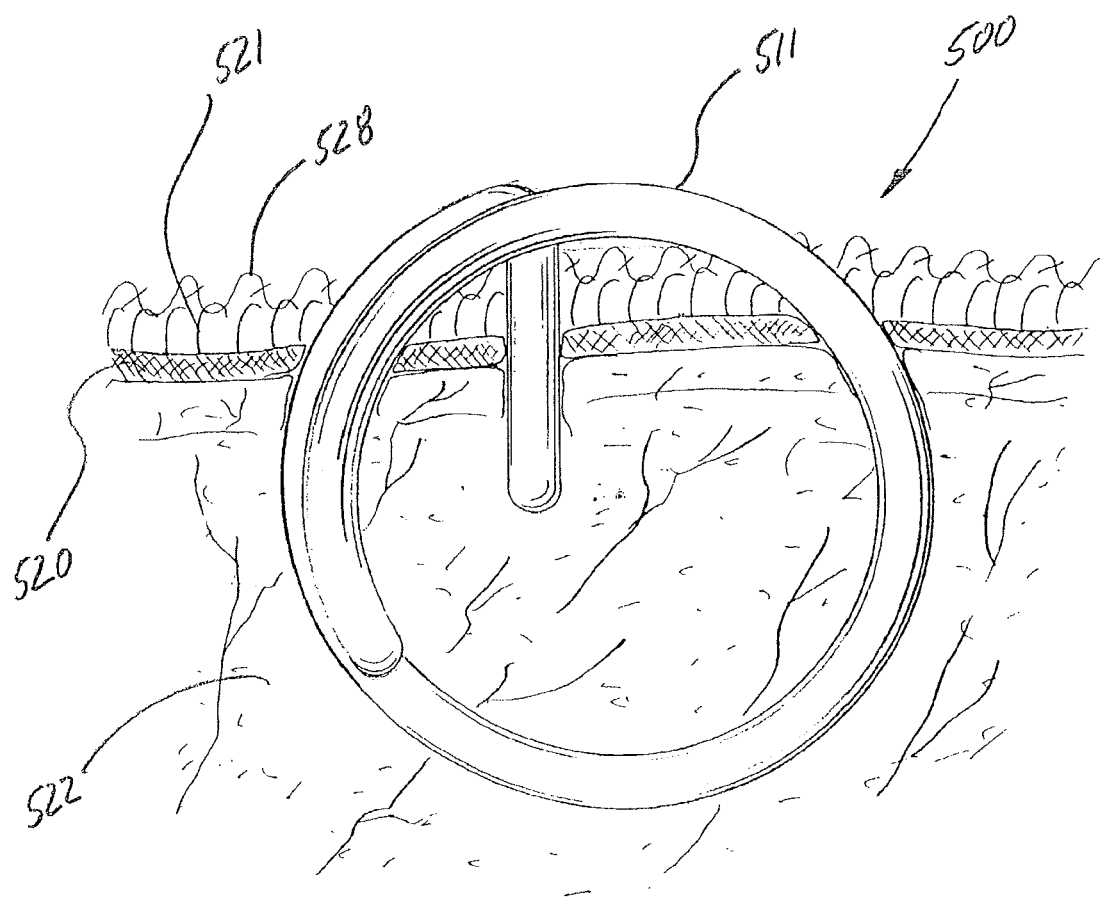
FIG. 8 is an enlarged, fragmentary front elevational view depicting the releasable mesh engagement element held in place with a Q-ring type of tack.

The foregoing description is to be taken as illustrative, but not limiting of the scope of the present invention. Still other variants within the spirit and scope of the present invention will readily present themselves to those skilled in the art such as, for example, the alternate article 500 shown in FIG. 8 where a patch or strip 520 including Velcro® type hook material 521 is positioned against the tissue 522 and a Q-ring type tack 511 of the type manufactured by Onux Medical, Inc. of Hampton, N.H. is driven through the patch 520 and into the tissue 522 to fasten the patch 520 to the tissue. It is understood, of course, that a plurality of patches such as patch 520 are positioned around the hernia site, and that a plurality of the tacks 511 are driven through the patches 520 respectively. The mesh 528 is then releasably securable to the aforesaid plurality of patches in the same manner as that described above with respect to the tacks 11.

What I claim is:

1. A method of positioning and securing a sheet of mesh material over tissue comprising:
    (a) securing a plurality of tacks to the tissue, each of the tacks having a mesh engagement element associated therewith;
    (b) positioning the sheet of mesh material over the tissue and the tacks;
    (c) pressing the sheet of mesh material against the tacks and the mesh engagement elements thereon; and
    (d) adjusting the position of sheet of mesh material over the tissue by releasably engaging and disengaging the sheet of mesh material from the mesh engagement elements.

2. The method of claim 1 wherein securing the plurality of tacks to the tissue includes positioning a plurality of the mesh engagement elements to the tissue and then driving a plurality of the tacks through the mesh engagement elements and into the tissue.

3. The method of claim 1 further comprising fastening the sheet of mesh material to the tissue following adjusting the position of sheet of mesh material over the tissue by releasably engaging and disengaging the sheet of mesh material from the mesh engagement elements.

4. A method of relieving tension of a damaged tissue comprising:
    (a) engaging a number of physiologically compatible tacks with physiology proximate the damaged tissue;
    (b) engaging a mesh with a head of each tack positioned on one side of the damaged tissue;
    (c) tensioning the mesh across the damaged tissue and engaging the mesh with a head of a tack positioned on another side of the damaged tissue; and
    (d) adjusting the tension of the mesh by repositioning the mesh relative to one of the tacks such that the mesh transfers a load away from the damaged tissue to the number of tacks.

5. The method of claim 4 wherein the physiology proximate the damaged tissue is muscle tissue.

6. The method of claim 4 further comprising passing a number of tacks through the mesh after the tension of the mesh has been adjusted such that the mesh is positioned between a number of tacks.

7. The method of claim 4 wherein engaging the number of tacks with physiology includes rotating each tack relative to the physiology.

8. The method of claim 4 further comprising adjusting the tension of the mesh by repositioning the mesh relative to a number of tacks such that the tension of the mesh can be adjusting in a first direction and a crossing direction.

9. A method of repairing a rupture comprising:
engaging a number of tacks with tissue proximate the rupture;
placing a mesh proximate the number of tacks;
engaging the mesh with a first tack;
tensioning the mesh toward a second tack;
engaging the mesh with the second tack to maintain the tension of the mesh; and
wherein the mesh is repositionable with respect to the tacks by pulling the mesh in a direction generally opposite the tension and without moving the tacks relative to the tissue.

10. The method of claim 9 wherein the mesh removably engages a side of the tacks generally opposite the tissue.

11. The method of claim 9 further comprising closing an opening in a patient that is formed to allow passage of the tacks and the mesh therethrough and sized to allow laparoscopic repair of the rupture.

12. The method of claim 11 further comprising passing the tacks through the opening and engaging the tacks with the tissue prior to positioning the mesh generally across the rupture.

13. The method of claim 9 further comprising passing a number of openings formed in the mesh over a number of hooks formed on a surface of each tack that is generally opposite a surface of the tack facing the tissue.

14. The method of claim 9 further comprising passing a barb of a supplemental tack through the mesh and into engagement with the tissue after the mesh has been secured by the first and second tacks.

15. The method of claim 9 wherein engaging the tacks with the tissue includes rotating the tacks about an axis that is generally perpendicular to the tissue.

16. The method of claim 15 further comprising engaging a tool with a tack driver cavity formed in a portion of the tack so that rotating a portion of the tool rotates the tack.

17. The method of claim 9 further comprising removing the mesh and the tacks upon repair of the tissue that resulted in the rupture.

* * * * *